United States Patent [19]

Holly

[11] 4,030,830
[45] June 21, 1977

[54] PROCESS AND APPARATUS FOR SENSING DEFECTS ON A SMOOTH SURFACE

[75] Inventor: Sandor Holly, Falls Church, Va.

[73] Assignee: Atlantic Research Corporation, Alexandria, Va.

[22] Filed: Jan. 5, 1976

[21] Appl. No.: 647,264

[52] U.S. Cl. .............................. 356/109; 250/563; 250/572; 356/120; 356/200; 356/237

[51] Int. Cl.² ........................................ G01B 9/02

[58] Field of Search ............... 356/102, 103, 106 R, 356/109, 111, 120, 121, 200, 237; 250/562, 563, 572

[56] References Cited

UNITED STATES PATENTS

| 3,680,961 | 8/1972 | Rudd | 356/102 |
| 3,782,827 | 1/1974 | Nisenson et al. | 356/120 |
| 3,953,128 | 4/1976 | Holly | 356/106 R |

Primary Examiner—John K. Corbin
Assistant Examiner—Matthew W. Koren
Attorney, Agent, or Firm—Martha L. Ross

[57] ABSTRACT

Method and apparatus for sensing the effective magnitude and/or number and/or position of individual depression and/or protrusion defects on a high-precision smooth surface of an article which may have said defects randomly distributed and relatively spatially distant each from the other, comprising continuously scanning the surface with a laterally-moving interference fringe pattern adjusted in size to have a cross-sectional area substantially smaller than the surface and no larger than an area which includes about an average predetermined spatial incidence of about one defect per pattern area; adjusting the fringe period to a size substantially larger than the effective cross-sectional dimension of a predetermined, maximum size defect; continuously sensing the AC and DC or AC signal components of the backscattered light; and substantially determining the effective magnitude and/or number and/or surface position of said defects by determining the magnitude of the AC or AC and DC signals obtained at each instantaneous relative position of the fringe pattern and the smooth surface. Said scan can thus provide information as to effective magnitude, number of defects, and topography of the defects on the surface. By the use of appropriate electronics, the information can be recorded and/or displayed.

68 Claims, 5 Drawing Figures

PROCESS AND APPARATUS FOR SENSING DEFECTS ON A SMOOTH SURFACE

BACKGROUND OF THE INVENTION

There has been a long-felt need for rapidly and accurately sensing the magnitude and/or number of depression and/or protrusion defects, particularly for quality control, on surfaces which require utmost smoothness for precision operation, as, for example, in the case of high quality optical devices, e.g. mirrors and lenses, semi-conductor wafers, and the like. Hitherto such sensing has generally been done manually and visually by operator scanning with a microscope or electron microscope. Such procedures have been found to be both slow and insufficiently precise in providing the desired information.

Laser Doppler velocimeters (LDV) have recently been developed for determining the rate of fluid flow in wind and fluid tunnels by suspending small particles in the fluid and determining their velocity and size by means of the velocimeter. Such velocimeters generally comprise convergent laser beams of equal size, intensity, and frequency which produce a stationary interference fringe pattern within the zone of convergence, sometimes called the probe volume. The interference fringes are planes which are normal to the plane defined by the center lines of the two converging laser beams and parallel to the bisector of the converging beams. In operation, the apparatus is set up to determine visibility in terms of the AC/DC ratio of the scattered light. The fluid-borne particles move across the fringes in trajectories normal to the fringe planes and normal to the converging beam bisector, thus crossing the fringe zone from the peripheral region of least intensity through the center region of maximum intensity, and then through the region of decreasing intensity. For optimum signal and resolution, the scattered-light collecting optics must be focused at or near the geometric center of the probe volume and, because of the rapid movement of the particle across it, the scattered radiation due to the particle generally consists of only a short burst in the order of microseconds. The number density of the particles passing through the stationary fringe pattern vary with consequent variation in the visibility bursts. The number can not be determined except on the basis of a hypothetical visibility equation which assumes that all of the particles are of substantially the same predetermined size. Such laser Doppler velocimeters are described in detail in the article by W. M. Farmer, "Measurement of Particle Size, Number Density, and Velocity Using a Laser Interferometer," Applied Optics, Vol. 11, No. 11, Nov. 1972, pp. 2603–2612, and G. J. Rudd, U.S. Pat. No. 3,680,961.

In more recent development of the Laser Doppler Velocimeter, the art discloses the use of probe volumes in which the fringes are caused to move continuously in a direction normal to the fringe planes by employing converging laser beams of the same intensity but slightly different frequency, e.g., a frequency difference within the radio frequency band. Such shifting of the frequency of one of the beams can, for example, be produced by diffraction of an incident laser beam by means of an ultrasonic Bragg cell, which can be made to divide the incident beam into two diverging beam components of the same intensity, one nondiffracted component having the incident beam frequency and the other diffracted component having its frequency shifted by an amount equal to the Bragg cell frequency. The difference in frequency between the two beams ($\Delta f$) is within the radio frequency band. Since the two coherent light beams which leave the Bragg cell are diverging, it is required that the beams be converged by an appropriate optical system to form the desired interference fringe pattern. The moving fringe pattern moves at a rate equal to $\Delta f$, which in turn is equal to the Bragg cell frequency.

The moving fringe technique has been applied to the LDV primarily to provide a means for determining the direction of movement of the particles moving across the fringe planes. It provides no substantial improvement in determination of particle size. The application of single and two-dimensional Bragg cell systems to the LDV is disclosed in Chu et al, "Bragg Diffraction of Light by Two Orthogonal Ultrasonic Waves in Water", Appl. Phys. Lett., Vol. 22, No. 11, 1 June 1973, pp. 557–59; and W. M. Farmer et al, "Two-Component, Self-Aligning Laser Vector Velocimeter," Applied Optics, Vol. 12, No. 11, Nov. 1973, pp. 2636–2640.

W. M. Farmer, "Observation of Large Particles with a Laser Interferometer," Applied Optics, Vol. 13, No. 3, March 1974, is primarily concerned with verifying experimentally certain of the theoretical predictions made by Farmer, Nov. 1972 supra. On page 616, col. 2, line 20, to page 618, col. 1, line 3, he concerns himself with experiments to test the validity of Eq. (28) in Farmer, Nov. 1972, as an assumed means for determining particle density from visibility. Eq. 28 (which is derived from Eq. (26), same reference) assumes that $$\overline{V}_n = \overline{V} / \sqrt{n}$$

where $\overline{V}$ is the ensemble average one-particle visibility function for the size distribution of the n particles. Visibility $V$ is defined in Equation 13 (same reference) as the AC/DC ratio. Farmer, March 1974, randomly mounts 10–15$\mu$ glass spheres onto a glass plate which he positions in the x–y plane of a moving fringe pattern adjusted to a $\lambda_s = 120\mu$. He checks the plates for regions where the scattered light indicates relatively high or low concentrations of particles positioned within the given cross-sectional fringe pattern area and then examines a stationary plate position with a spatially-stationary fringe spot. For an indication of concentrations which Farmer considers high or low, see FIG. 11, page 620 where the number of particles derived from 10 separate stationary glass plate visibility measurements vary from 43 ± 20 to 308 ± 148. Based on the Farmer approach, the number must be determined with prior knowledge of particle size and, according to Farmer, "(the visibility measurement is strictly valid only for monodisperse sizes)." It is clear, therefore, that Farmer is concerned only with attempting (within an exceedingly wide margin of error) to determine from a single integrated visibility signal the number of particles of essentially the same, known size within a given, spatially-stationary fringe pattern cross-sectional area. The difficulty of such an undertaking is obvious from such factors as the probabilty that the signals of at least a substantial number of the particles may be cancelled out by the random distribution which will place some in light and in dark areas of the fringe zone and signal attenuation produced by individual particle distance from the geometric center of the fringe pattern. It is clear, therefore, that Farmer, March 1974, does not and indeed cannot teach or suggest applicant's process or apparatus, and, in fact, given his requirement for preknown, monodisperse sizes, teaches away from it.

None of the available art recognizes or discloses the present invention, its principle of operation or its use in sensing the effective magnitude of unknown, differently-sized depression and/or protrusion defects, the number of such defects, or the geographical distribution (topography) of such defects on a high-precision, smooth surface, or the presence and size of scattered "rough" spots on the precision surface.

SUMMARY OF THE INVENTION

The invention comprises a process (and apparatus therefor) for sensing the effective magnitude and/or number and/or spatial distribution of individual depression (e.g. scratch) and/or protrusion (e.g. ridge) defects on a high-precision smooth surface of an article which may have such defects randomly distributed and relatively spatially-distant each from the other and which may additionally have inadvertent, relatively spatially-distant rough spots comprising adjacent randomly distributed defects. The desired results are obtained by a. providing a laser source; b. dividing the coherent laser beam into two coherent beams of equal size and intensity which differ in frequency, the difference $\Delta f$ being within the radio frequency band; c. converging the two beams to form within the volume of convergence an interference fringe pattern zone; d. adjusting the cross-sectional area of the fringe pattern in the $x-y$ plane so that it is substantially smaller than the smooth surface to be scanned and no larger than an area which includes about an average predetermined spatial incidence of about one defect per pattern area on said surface; e. adjusting the fringe period $\lambda_s$ of the pattern to a width which is substantially wider than (preferably at least twice as wide as) the effective cross-sectional dimension of a predetermined, maximum-size defect as indicated by backscatter signal magnitude; f. positioning at least the portion of the article bearing the smooth surface within the fringe pattern in such manner that the smooth surface lies substantially in a plane defined by the $x$ and $y$ axes of the fringe pattern and the angle of incidence of the bisector of the pair of converging beams forming the fringe pattern is at an angle relative to said surface at the point of incidence such as to provide an angle of specular reflection, whereby substantially all specularly-reflected radiation bypasses the receiver of the backscattered optical radiation; g. continuously spatially displacing the fringe pattern and/or the smooth surface relative to each other while maintaining the relative orientation of the surface and the fringe pattern as defined above; h. continuing the relative displacement in such manner that the entire predetermined area of the smooth surface or sufficient area to determine the presence of unacceptable defects is scanned by the fringe pattern; i. as the relative displacement continues, continuously sensing the AC and DC signal components of the backscattered radiation, wherein, at any given instantaneous moment of scan:

1. in the case comprising sensing of a single defect within the cross-sectional area of the fringe pattern:
   aa. substantially zero AC and DC signals indicate smooth, defect-free surface;
   bb. a substantially zero AC signal and a substantially non-zero DC signal indicate an effective defect width substantially at least as wide as $\lambda_s$;
   cc. substantially non-zero AC and DC signals wherein the AC/DC ratio is substantially equal to one indicate the presence of a defect, the effective width of which is proportional to the AC and DC signal amplitudes and substantially less than the width of $\lambda_s$;
   dd. substantially non-zero AC and DC signals wherein the AC/DC ratio is substantially less than one indicate a defect, the effective width of which is approaching $\lambda_s$; and
   ee. the amplitude of the non-zero AC signal and/or the ratio of the AC/DC signal indicate the effective cross-sectional width of the defect; and 2. in the case comprising the possible presence of a plurality of adjacent, relatively small, randomly-positioned and -sized defects within the cross-sectional area of the fringe pattern, wherein:
   aa. a substantially zero AC signal and a substantially non-zero DC signal are obtained; or
   bb. substantially non-zero AC and DC signals are obtained, wherein the AC/DC ratio is substantially less than 1;

a DC signal larger than a first predetermined value indicates the presence of said plurality and a DC signal having a second predetermined value may be used as a threshold indication of the acceptability of the defect.

By the use of suitable electronics, position of a defect at any given distance of displacement of the smooth surface relative to the pattern can be determined and the following information can be recorded and/or displayed: effective cross-sectional dimension of the defect along the y axis as defined by signal magnitude, the number of defects, and the topographical position of the defects on the surface.

The term "effective" magnitude, dimension, or width as employed herein, in the specification and claims, is an integration of a number of characteristics of the defect which affect the amount or intensity of backscatter. These include, in addition to the actual width of the defect in the y direction, such factors as the surface shape and fine structure, namely the severity of the defects. For example, a shallow depression will produce a backscatter signal of lesser magnitude than a deep depression having essentially the same cross-sectional dimension. The former may be acceptable for the particular application and the latter unacceptable. Thus given a predetermined threshold (acceptable vs. unacceptable) backscatter signal magnitude (which will be discussed in greater detail below), the process and means of the invention provide a finely-tuned, accurate, and rapid scan for unacceptable defects on a high-precision smooth surface.

Meaningful application of the invention requires some preliminary knowledge concerning the smooth surface of the particular surfaces to be examined, such as quality requirements in terms of spatial incidence and maximum acceptable size and severity of defects. Much process requirement information can be obtained by preliminary scannings and calibrations of the surfaces of a given type, such as average spatial incidence, average maximum defect severity, e.g. size and contour characteristics. Such preliminary scannings can be compared with information available from other means, such as microscopic examination.

Adjustment of the cross-sectional area of the fringe pattern in the $x-y$ plane so that it is substantially no larger than an area which includes an average, predetermined spatial incidence of about one defect per pattern area on the smooth surface, is of importance in determining accurately defect number, effective size, and position since a single backscatter signal is received at any instantaneous moment of scan regardless of the number and effective size of the defects in the cross-sectional area of the fringe pattern. Since the defects on a high-precision surface are generally relatively widely spaced, though random, precalibration for a given application can be employed to determine the pattern size to be used. Because of the random distribution, occasionally more than one defect, e.g. two, may appear in an instantaneous area of the fringe pattern. Accurate resolution between the two can generally be made by observation of signal magnitude changes as the fringe pattern is translated relative to the surface, thereby eliminating one of the defects in a subsequent instantaneous area of scan.

Fringe pattern size is primarily a function of the width of the two convergent beams, which in turn is a function of the width of the laser beam. Thus pattern size for a given laser can be adjusted by such conventional means as positioning a divergent or convergent optical means, e.g. a lens, in the path of the laser beam prior to splitting it into the two coherent light beams or in the path of each of the equally split beams.

Width of the fringe period $\lambda_s$ should be substantially wider than the predetermined maximum effective cross-sectional dimension of the imperfections (effective dimensions being determined by the amplitude of the AC signal or AC/DC signal ratio which will be discussed more fully below). Preferably it is at least twice as wide. The fringe period is a known quantity since it can be determined by conventional techniques from such factors as laser wavelength and angle of convergence $\theta$ of the beams. Adjustment of the system to provide a given fringe period can be accomplished in various ways as, for example, by changing the input laser wavelength. Generally, it is most easily achieved by adjusting the convergent angle of the beams by such conventional means as shifting the converging optics along the z axis or by changing the RF frequency of the $\Delta f$-producing means, such as a Bragg cell.

A substantial difference in width between the fringe period and the maximum-expected effective width (as determined by the magnitude of the AC backscatter signal and/or the AC/DC ratio magnitude) is essential to obtain adequately resolvable AC signal magnitude either per se or in relation to the DC signal in order to determine accurately the effective defect size. Both AC and DC substantially zero backscatter signals indicate smooth surface substantially free from defect. A substantially zero AC signal and a substantially non-zero DC signal indicate an effective defect width as wide or wider than $\lambda_s$. Substantially non-zero AC and DC signals wherein the AC/DC ratio is substantially equal to one indicate the presence of a defect, the effective width of which is proportional to the AC and DC signal amplitudes and substantially less than $\lambda_s$. In this regime, the AC and DC backscatter signals increase in relation with increase in effective defect width. Such proportionality is most generally found within a ratio of effective defect width to $\lambda_s$ of up to about $\lambda_s/2$, preferably less. Within this proportionality regime, it is most convenient and may be more accurate to determine effective defect width by sensing the amplitude of the AC backscatter signal alone. As effective defect size approaches $\lambda_s$, namely becomes progressively larger than about $\lambda_s/2$, AC signal begins to decrease in amplitude and the DC signal progressively increases in magnitude, resulting in an AC/DC ratio progressively decreasing toward zero value and the AC/DC ratio signal provides a more accurate indication of effective defect width.

In some cases, in addition to relatively spatially-distant individual defects, a high-precision smooth surface may have spots of inadequately polished or otherwise smoothed surface, namely inadvertent rough spots which essentially comprise numerous adjacent, randomly scattered, relatively small defects, which may or may not be acceptable for a given application. Since such rough spots appearing during scan within the pattern area produce single magnitudes of AC and DC signals at each instantaneous area of scan, it may be necessary, depending on the magnitude of the signals, to distinguish such a spot from a single defect. This can be accomplished by comparing the magnitude of the DC signal obtained with the predetermined maximum DC signal for the particular application obtained from maximum expected single defect cross-sectional dimension. A higher observed DC signal magnitude indicates a rough surface, the total effective width of which is determinable from the continuing scan. Although the size of the individual imperfections cannot be accurately determined, quality acceptability can be established by predetermination of a maximum or threshold DC signal magnitude for any such rough spots found.

It is generally essential to avoid the inclusion of any specular radiation with backscatter radiation gathered by the collecting optics and receiver, e.g. a photomultiplier tube (PMT). The high level of specularly reflected light in relation to the much lower level of light backscattered from imperfections saturates the detector or, at least, causes unacceptably noisy signals. Interception of specular reflected component by the receiver can be avoided by ensuring that the angle of incidence of the bisector of the pair of converging beams forming the fringe pattern is at an angle relative to the smooth surface at the point of incidence such as to provide an angle of specular reflection whereby substantially all specularly-reflected radiation bypasses the receiver of the backscattered optical radiation. This can be accomplished by positioning the receiver so that it is outside the range of specularly-reflected radiation. In some cases, for convenience and latitude in positioning the receiver, it may be desirable to tilt the smooth surface somewhat around the y axis of the pattern to change the angle of incidence of the beam bisector and thereby the angle of reflection of the specular radiation, as shown for example, in FIGS. 1 and 4.

The fringe pattern area, which, as aforedescribed, is very substantially smaller than the area of the smooth surface, and the surface are continuously displaced relative to each other to produce a scan of the entire smooth surface area or cover an area of the surface sufficient to indicate the presence of unacceptable defects. The scan can be of the rectangular raster type which can be accomplished by means of a spatially stationary fringe pattern and a conventional x–y continuously movable stage attached to the article bearing the smooth surface being tested; or by oscillating the fringe pattern as, for example, by means of oscillating mirror over a relatively small degree of arc around the x axis of the pattern in combination with a x-stage, attached to the article, which moves incrementally in the y direction as each scan across the y direction of the smooth surface is completed. The scan can also be made helical or spiral by using a suitable combination of conventional rotary and translation stages.

To scan the entire surface, it is, of course, essential that at different levels (in the y direction) of the scan, the perimeter of the fringe at least abut the fringe perimeter of the previous scan level. For somewhat more accurate single defect resolution, e.g. where more than a single defect exists in an instantaneous moment of scan in an adjacent position of the prior level of scan, it may be desirable to overlap the pattern peripheries.

In some cases, it may be desirable to do a second scan across the same surface turned 90° with respect to its earlier orientation to ensure adequate resolution of defects which are long in the y direction. This may be desirable, for example, where the effective cross-sectional width of a particular defect(s) in the y direction is actually the length of the defect and therefore extends up to or beyond the size of $\lambda_s$. Such a second scan can also be accomplished by rotating the plane of the converging beams to a second angular orientation usually 90° with respect to its earlier orientation.

Figure 5:
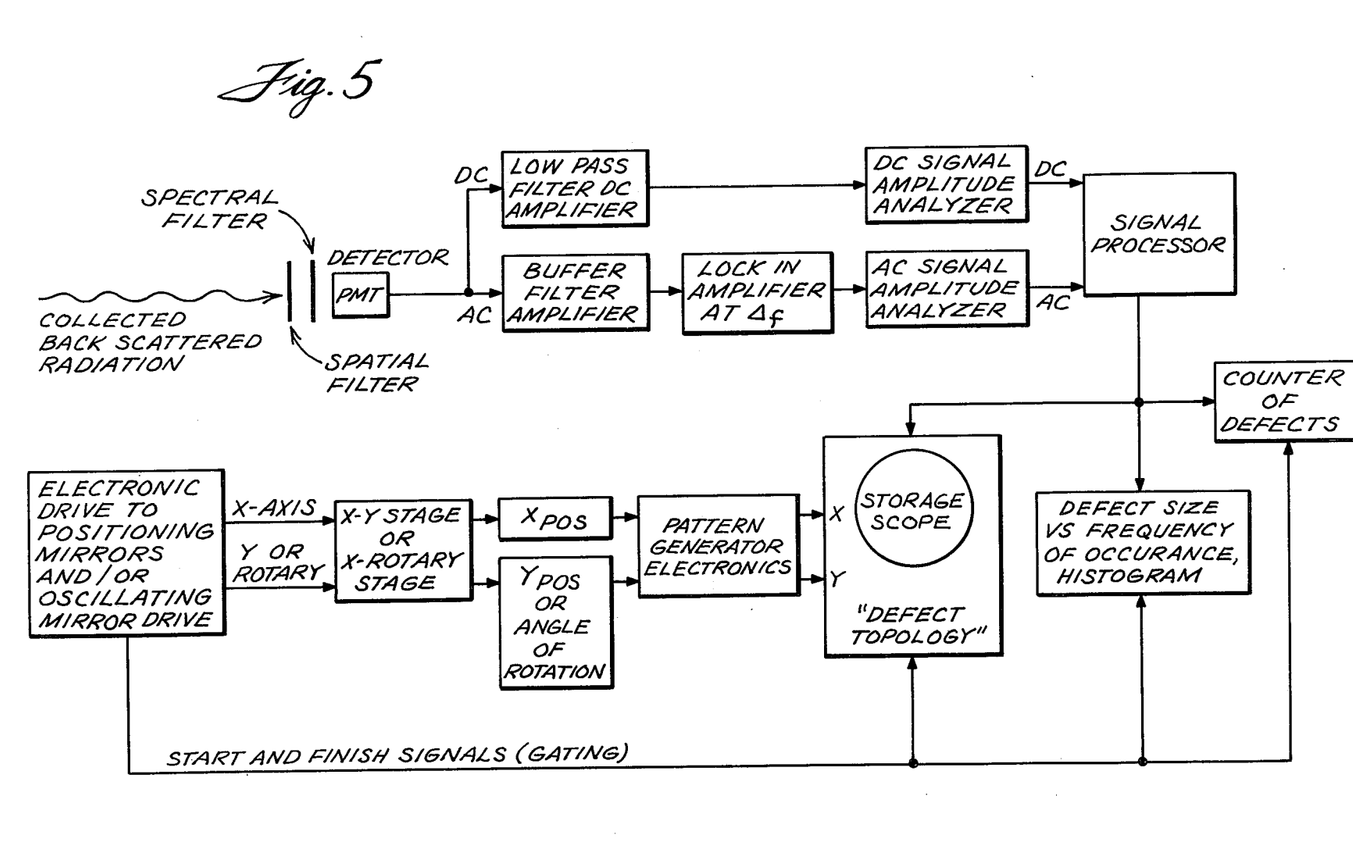
FIG. 5 is a schematic illustration of components which can be used for the "electronics" system.

Processing of the backscattered radiation reaching the receiver and the AC and DC signal components of the radiation can be accomplished by conventional electronics, as illustrated in FIG. 5. By means of appropriate electronics, the effective cross-sectional dimension of succeeding defects as defined by signal magnitude can be recorded and/or displayed, their number counted, and their size vs. frequency shown, as, for example, by means of a histogram. The position of the defect on the smooth surface can also be recorded and/or displayed by means of suitable electronics, such as a storage scope.

Although a principal use of the invention is with smooth planar surfaces, it can also be used with convex or concave, spherical or cylindrical surfaces. In the case of such curved surfaces, the x-y plane position is set by a plane determined by the convergent beams bisector and the center of curvature of the surface, which for a spherical surface is a point and for a cylindrical surface is the longitudinal axis of the cylinder. In the course of the scan, the tangent to the point of incidence of the bisector is maintained substantially in the x-y plane of the pattern. If necessary, the tangential plane at the point determined by the bisector intercepting the spherical or cylindical surface is tilted with respect to the x-y plane of the fringe pattern by an angle sufficient to avoid specular reflection to the receiver. Movable stages to provide the desired relative position of scan include rotary and translational tables.

It will be understood that the components for the apparatus for carrying out the process of the invention, including the optics and associated electronics, are conventional state-of-the-art.

DETAILED DESCRIPTION

Figure 1:
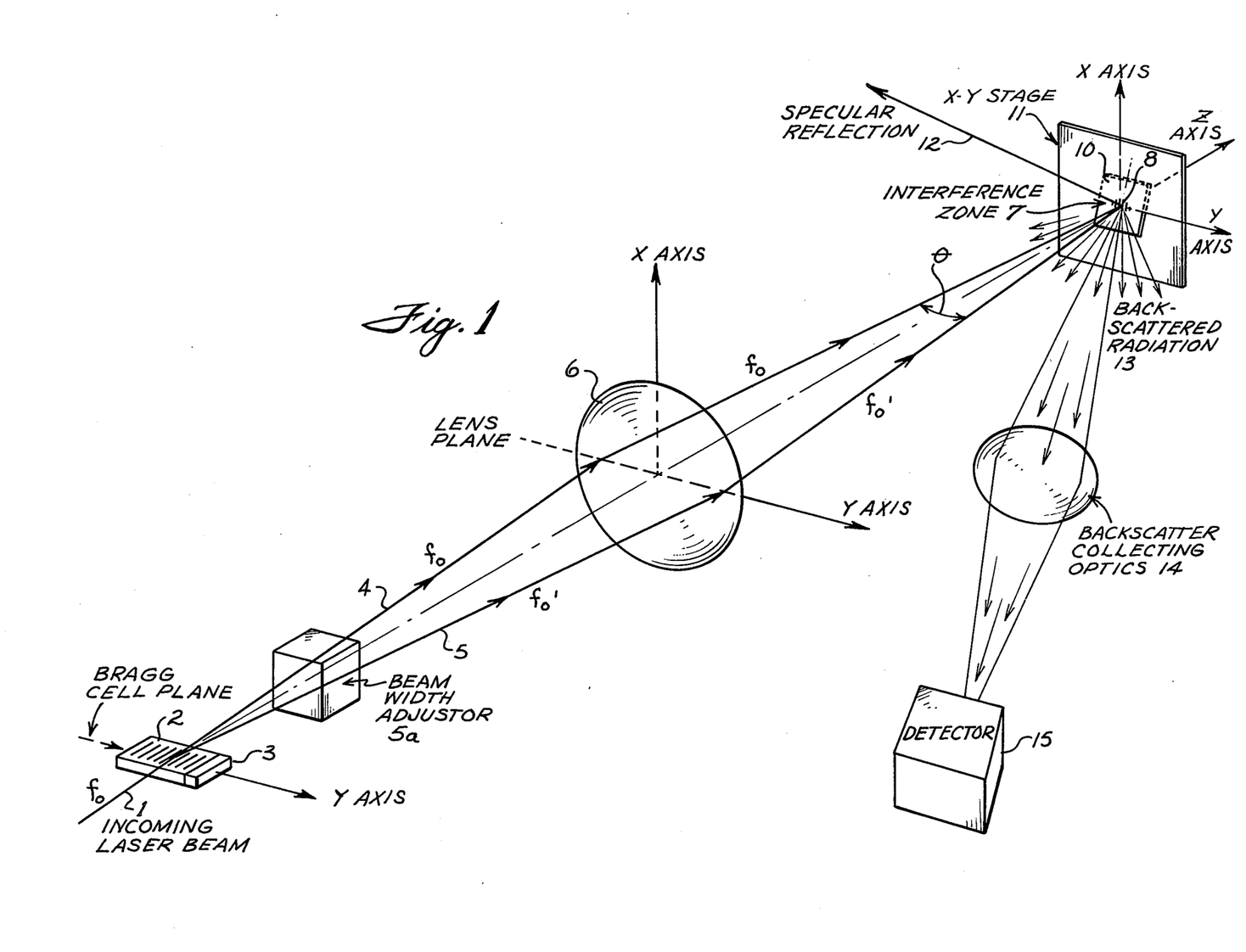
FIG. 1 is a diagrammatic illustration showing one embodiment of an optical system for implementing the defect monitoring system of the invention and the coherent light beam paths and relationships.
Figure 2:
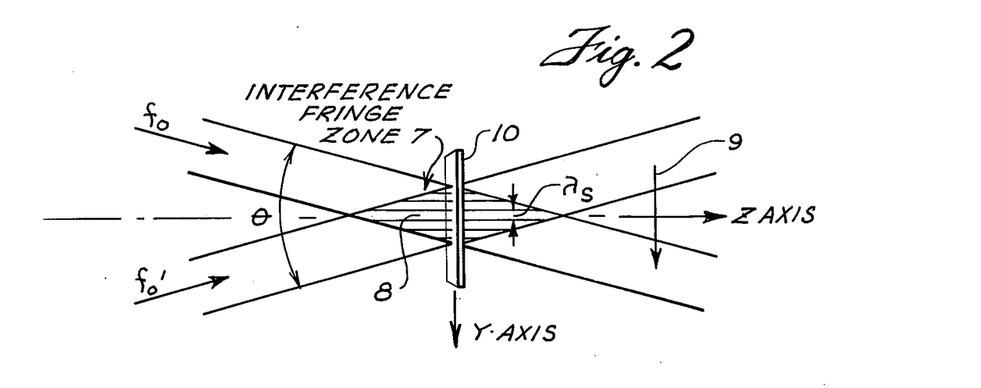
FIG. 2 is an enlarged diagrammatic illustration showing the crossover of the converging coherent light beams and resulting moving interference fringe zone shown in FIG. 1.
Figure 3:
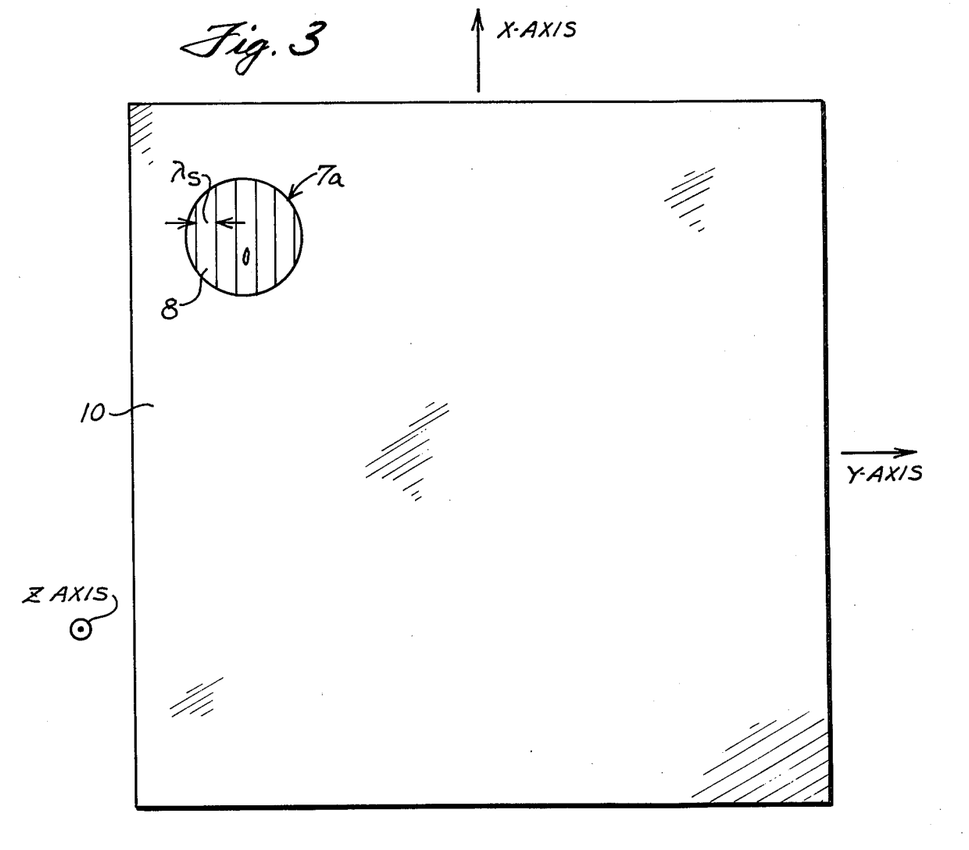
FIG. 3 is a schematic illustration showing the fringe pattern area on the surface at an instantaneous moment in relative translation.

In FIG. 1, laser beam 1 of frequency $f_o$ enters at a slight angle, diffraction Bragg cell 2 which consists of an acoustic medium and is compressionally driven by crystal transducer 3 at an imposed oscillation frequency, e.g., 10 to 100 Mc, to form acoustic wavelengths $\lambda_a$ in the cell medium. The input laser beam is divided by the Bragg cell into two coherent light beams of equal intensity, one beam 4 being non-diffracted and having the original $f_o$ frequency, and the other beam 5 being diffracted and acoustically modified into slightly shifted frequency $f_{o'}$. The difference in frequency $\Delta f$ is within the radio frequency range and equals the RF Bragg cell frequency. Beam adjuster 5a, e.g. a beam expander, is employed to change the width of the convergent beams. The diverging beams leaving the cell are passed through appropriately designed convex lens 6, which converges the beams at cross-over zone 7 to form a fringe pattern 7a (FIG. 3) at an angle of convergence $\theta$. Within the zone of convergence a pattern of alternating dark and light regions, i.e. interference fringes 8, shown out of proportion in FIG. 1, but more clearly defined in FIG. 2. The fringes move in the direction shown by arrow 9 at a rate equal to $\Delta f$. FIGS. 1 and 2 show the relative positions of the x, y, and z axes of the various components. It will be seen that the y and z axes lie in the plane of the paper and the x axis lies perpendicular to the paper. The bisector of the two diverging-converging $f_o$ and $f_{o'}$ beams produced by the Bragg cell lie along the z axis; the normal to the fringe planes (y axis) is perpendicular to the converging beam bisector (z axis), the fringe planes are in the x-z plane; and the fringes move in the y direction. Smooth surface 10 is positioned and held on x-y stage 11 within the fringe zone, so that it lies substantially in the x-y plane with a small degree of tilt around the y axis. As shown schematically, the fringes move transversely across the surface in the y direction.

The fringe period $\lambda_s$ is determined by the equation:

$$\lambda_s = \frac{\lambda_o}{2\sin(\theta/2)}$$

where $\lambda_o$ is the wavelength of the incident laser beam. It is obvious, therefore, that the size of the fringe period $\lambda_s$ can be varied either or both $\lambda_o$ and $\theta$. In general, it is easier to vary $\lambda_s$ by adjusting the convergent beam angle $\theta$, as for example by changing the optical magnification, i.e. shifting the position of the converging lens along the z axis, by changing the acoustic frequency of the Bragg cell, or by mechanical movements of additional optical components, or by a combination of the foregoing methods.

Arrow 12 shows the direction of specular reflections of the bisector caused by the tilt of surface 10. Backscatter radiation 13 is collected by collecting optics 14 and received by detector 15, which may, for example, be a PMT.

Figure 4:
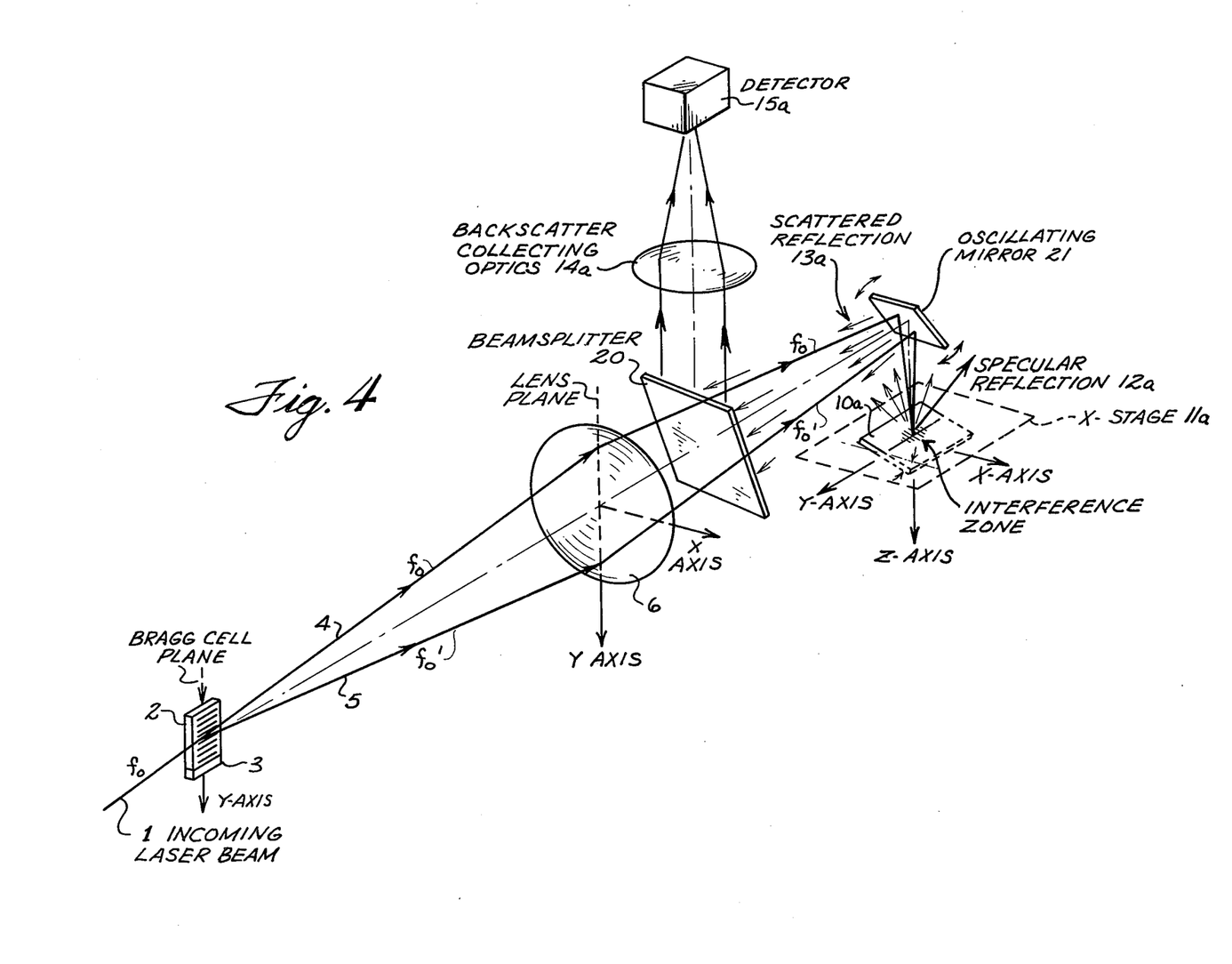
FIG. 4 is a schematic illustration of a modified system.

FIG. 4 shows a modified embodiment of the invention wherein the beams 4 and 5 are rotated through a 90° angle by rotation of Bragg cell 2 thereby changing the directions of the x, y, and z axes with respect to the plane of the paper as shown. After passing through converging lens 6 the converging $f_o$ and $f_{o'}$ beams pass through beam splitter 20 which produces a 50:50 split in the beams, half of which (not shown) are dumped and the other half of the beams continue to mirror 21 tilted at about a 45° angle to the bisector.

Mirror 21 oscillates through an arc, which may, for example, be about 42° to 48′ and focuses the converging beams $f_o$ and $f_o$', onto smooth, tilted surface 10a positioned as aforedescribed (FIG. 1) in the fringe pattern. Since the oscillating mirror scans the smooth surface in a straight line across the surface in the y direction, the stage 11a bearing the article moves incrementally in the x direction in synchronization with completion of a y direction scan. Specular reflection 12a is in a direction determined by the angle of incidence of the beams bisector with respect to the normal of the surface. Backscatter radiation 13a, free from specular reflection, is reflected by mirror 21 to tilted beam splitter 20 which, in turn, reflects half of it to collecting optics 14a and to detector 15a.

FIG. 5 illustrates schematically associated electronics, which are adequately defined in the legends.

It will be understood that different optical and electronics means known to the art can be employed to practice the invention.

Although this invention has been described with reference to illustrative embodiments thereof, it will be apparent to those skilled in the art that the principles of this invention can be embodied in other forms but within the scope of the claims.

I claim:

1. A process for sensing the effective magnitude and/or number and/or spatial distribution of individual depression and/or protrusion defects on a high-precision smooth surface of an article which may have said defects randomly distributed and relatively spatially-distant each from the other and which additionally may have relatively spatially-distant rough spots comprising adjacent randomly-distributed defects, comprising:
   a. producing two coherent optical radiation beams of the same intensity, one of said beams having a different frequency from said other beam, the frequency difference Δf being within the radio frequency range;
   b. converging said beams to form an interference zone comprising a fringe pattern within the zone of convergence, said fringe pattern continuously moving laterally at a rate equal to Δf;
   c. adjusting the cross-sectional area of the fringe pattern in the x–y plane so that it is substantially smaller than said surface and no larger than an area which includes about an average predetermined spatial incidence of about one defect per pattern area on said surface;
   d. adjusting the fringe period $\lambda_s$ of the pattern to a width which is substantially wider than the effective cross-sectional dimension of a predetermined, maximum-size defect as indicated by backscatter signal magnitude;
   e. positioning at least the portion of said article bearing said smooth surface within the fringe pattern in such a manner that said surface lies substantially in a plane defined by the x and y axes of the fringe pattern and the angle of incidence of the bisector of the pair of converging beams forming the fringe pattern is at an angle relative to said surface at the point of incidence such as to provide an angle of specular reflection, whereby substantially all specularly-reflected radiation bypasses a receiver of the backscattered optical radiation;
   f. continuously spatially displacing the interference zone and/or said smooth surface relative to each other while maintaining the relative orientation of said surface and said fringe pattern substantially as defined in (e) supra;
   g. continuing said relative displacement in such manner that substantially the entire predetermined area of said surface or sufficient area to determine the presence of unacceptable defects is scanned by said fringe pattern; and
   h. as said relative displacement continues, continuously sensing the AC and DC signal components of the backscattered radiation, wherein, at any given instantaneous moment of scan:
      1. in the case comprising sensing of a single defect within the cross-sectional area of the fringe pattern:
         aa. substantially zero AC and DC signals indicate smooth, defect-free surface;
         bb. a substantially zero AC signal and a substantially non-zero DC signal indicate an effective defect width substantially at least as wide as $\lambda_s$;
         cc. substantially non-zero AC and DC signals wherein the AC/DC ratio is substantially equal to 1 indicate the presence of a defect, the effective width of which is substantially proportional to the AC and DC signal amplitudes and substantially less than the width of $\lambda_s$;
         dd. substantially non-zero AC and DC signals wherein the AC/DC ratio is substantially less than 1 indicate a defect, the effective width of which is approaching $\lambda_s$; and
         ee. the amplitude of said non-zero AC signal and/or the ratio of said AC/DC signal indicate the effective cross-sectional width of said defect; and
      2. in the case comprising the possible presence of a plurality of relatively small, randomly positioned and sized defects within the cross-sectional area of the fringe pattern, wherein:
         aa. a substantially zero AC signal and a substantially non-zero DC signal are obtained; or
         bb. substantially non-zero AC and DC signals are obtained, wherein the AC/DC ratio is substantially less than 1;

a DC signal larger than a first predetermined value for a single defect indicates the presence of said plurality and a DC signal having a second predetermined value, may be used as a threshold indication of the acceptability of the defect.

2. The process of claim 1 wherein the magnitude of the AC signal and/or DC signal and/or AC/DC ratio are respectively compared with a predetermined magnitude of AC signal and/or DC signal and/or AC/DC ratio.

3. The process of claim 2 which includes the step of continuously recording and displaying information as to the magnitude of the AC signal and/or the DC signal and/or the AC/DC ratio and, thereby information as the effective cross-sectional dimension along the y axis of each defect.

4. The process of claim 3 which includes the step of continuously recording and/or displaying information as to the number of said defects on said smooth surface.

5. The process of claim 4 which includes the step of continuously recording and/or displaying information as to the number of said defects within given ranges of magnitude of said AC signal and/or DC signal and/or AC/DC ratio.

6. The process of claim 5 wherein the presence of a defect at a given distance of displacement of said smooth surface relative to the fringe pattern provides information as to the position of the defect on said surface.

7. The process of claim 6 which includes the step of continuously recording and/or displaying information as to the position of each defect on said surface.

8. The process of claim 4 wherein the presence of a defect at a given distance of displacement of said smooth surface relative to the fringe pattern provides information as to the position of the defect on said surface.

9. The process of claim 8 which includes the step of continuously recording and/or displaying information as to the position of each defect on said surface.

10. The process of claim 3 wherein the presence of a defect at a given distance of displacement of said smooth surface relative to the fringe pattern provides information as to the position of the defect on said surface.

11. The process of claim 10 which includes the step of continuously recording and/or displaying information as to the position of each defect on said surface.

12. The process of claim 2 wherein the presence of a defect at a given distance of displacement of said smooth surface relative to the fringe pattern provides information as to the position of the defect on said surface.

13. The process of claim 12 which includes the step of continuously recording and/or displaying information as to the position of each defect on said surface.

14. The process of claim 2 wherein $\lambda_s$ is adjusted to a width which is at least about 2 times wider than the effective cross-sectional dimension.

15. The process of claim 1 which includes the step of continuously recording and displaying information as to the magnitude of the AC signal and/or the DC signal and/or the AC/DC ratio and, thereby information as to the effective cross-sectional dimension along the $y$ axis of each defect.

16. The process of claim 15 which includes the step of continuously recording and/or displaying information as to the number of said defects on said smooth surface.

17. The process of claim 16 which includes the step of continuously recording and/or displaying information as to the number of said defects within given ranges of magnitude of said AC signal and/or DC signal and/or AC/DC ratio.

18. The process of claim 17 wherein the presence of a defect at a given distance of displacement of said smooth surface relative to the fringe pattern provides information as to the position of the defect on said surface.

19. The process of claim 18 which includes the step of continuously recording and/or displaying information as to the position of each defect on said surface.

20. The process of claim 16 wherein the presence of a defect at a given distance of displacement of said smooth surface relative to the fringe pattern provides information as to the position of the defect on said surface.

21. The process of claim 20 which includes the step of continuously recording and/or displaying information as to the position of each defect on said surface.

22. The process of claim 15 wherein the presence of a defect at a given distance of displacement of said smooth surface relative to the fringe pattern provides information as to the position of the defect on said surface.

23. The process of claim 22 which includes the step of continuously recording and/or displaying information as to the position of each defect on said surface.

24. The process of claim 1 wherein the presence of a defect at a given distance of displacement of said smooth surface relative to the fringe pattern provides information as to the position of the defect on said surface.

25. The process of claim 24 which includes the step of continuously recording and/or displaying information as to the position of each defect on said surface.

26. The process of claim 1 wherein $\lambda_s$ is adjusted to a width which is at least about two times wider than the effective cross-sectional dimension.

27. The process of claim 2 wherein said smooth surface is tilted around the $y$ axis through a degree of arc sufficient to ensure that substantially all specularly-reflected radiation bypasses the receiver of the back-scattered optical radiation.

28. The process of claim 1 wherein said smooth surface is tilted around the $y$ axis through a degree of arc sufficient to ensure that substantially all specularly-reflected radiation bypasses the receiver of the back-scattered optical radiation.

29. A process for sensing the effective magnitude and/or number and/or spatial distribution of individual depression and/or protrusion defects on a high-precision smooth surface of an article which may have said defects randomly distributed and relatively spatially-distant each from the other and which additionally may have relatively spatially-distant rough spots comprising adjacent randomly-distributed defects, comprising:

a. producing two coherent optical radiation beams of the same intensity, one of said beams having a different frequency from said other beam, the frequency difference $\Delta f$ being within the radio frequency range;

b. converging said beams to form an interference zone comprising a fringe pattern within the zone of convergence, said fringe pattern continuously moving laterally at a rate equal to $\Delta f$;

c. adjusting the cross-sectional area of the fringe pattern in the $x$–$y$ plane so that it is substantially smaller than said surface and no larger than an area which includes about an average predetermined spatial incidence of about one defect per pattern area on said surface;

d. adjusting $\lambda_s$ to a width which is at least about 2 times wider than the effective cross-sectional dimension of a predetermined, maximum-size defect as indicated by backscatter signal magnitude;

e. positioning at least the portion of said article bearing said smooth surface within the fringe pattern in such manner that said surface lies substantially in a plane defined by the $x$ and $y$ axes of the fringe pattern and the angle of incidence of the bisector of the pair of converging beams forming the fringe pattern is at an angle relative to said surface at the point of incidence such as to provide an angle of specular reflection, wherein substantially all specularly-reflected radiation bypasses a receiver of the backscattered optical radiation;

f. continuously spatially displacing the interference zone and/or said smooth surface relative to each other while maintaining the relative orientation of said surface and said fringe pattern substantially as defined in (e) surpa;

g. continuing said relative displacement in such manner that substantially the entire predetermined area of said surface or sufficient area to determine the presence of unacceptable defects is scanned by said fringe pattern; and h. as said relative displacement continues, continuously sensing the AC signal component of the backscattered radiation, wherein, at any given instantaneous moment of scan, in the case comprising sensing of a single defect within the cross-sectional area of the fringe pattern:
  1. a substantially zero AC signal indicates smooth, defect-free surface; and
  2. a substantially non-zero AC signal indicates the presence of a defect, the effective width of which is substantially proportional to the AC signal amplitude.

30. The process of claim 29 wherein the amplitude of the AC signal is compared with a predetermined amplitude of AC signal.

31. The process of claim 30 which includes the step of continuously recording and/or displaying information as to the amplitude of the AC signal and thereby information as to the effective cross-sectional dimension along the y axis of each defect.

32. The process of claim 31 which includes the step of continuously recording and/or displaying information as to the number of defects on said smooth surface.

33. The process of claim 32 which includes the step of continuously recording and/or displaying information as to the number of said defects within given ranges of amplitude of said AC signal.

34. The process of claim 33 wherein the presence of a defect at a given distance of displacement of said smooth surface relative to the fringe pattern provides information as to the position of the defect on said surface.

35. The process of claim 34 which includes the step of continuously recording and/or displaying information as to the position of each defect on said surface.

36. The process of claim 32 wherein the presence of a defect at a given distance of displacement of said smooth surface relative to the fringe pattern provides information as to the position of the defect on said surface.

37. The process of claim 36 which includes the step of continuously recording and/or displaying information as to the position of each defect on said surface.

38. The process of claim 31 wherein the presence of a defect at a given distance of displacement of said smooth surface relative to the fringe pattern provides information as to the position of the defect on said surface.

39. The process of claim 38 which includes the step of continuously recording and/or displaying information as to the position of each defect on said surface.

40. The process of claim 30 wherein the presence of a defect at a given distance of displacement of said smooth surface relative to the fringe pattern provides information as to the position of the defect on said surface.

41. The process of claim 40 which includes the step of continuously recording and/or displaying information as to the position of each defect on said surface.

42. The process of claim 30 wherein said smooth surface is tilted around the y axis through a degree of arc sufficient to ensure that substantially all specularly-reflected radiation bypasses the receiver of the backscattered optical radiation.

43. The process of claim 29 which includes the step of continuously recording and/or displaying information as to the amplitude of the AC signal and thereby information as to the effective cross-sectional dimension along the y axis of each defect.

44. The process of claim 43 which includes the step of continuously recording and/or displaying information as to the number of defects on said smooth surface.

45. The process of claim 44 which includes the step of continuously recording and/or displaying information as to the number of said defects within given ranges of amplitude of said AC signal.

46. The process of claim 45 wherein the presence of a defect at a given distance of displacement of said smooth surface relative to the fringe pattern provides information as to the position of the defect on said surface.

47. The process of claim 46 which includes the step of continuously recording and/or displaying information as to the position of each defect on said surface.

48. The process of claim 44 wherein the process of a defect at a given distance of displacement of said smooth surface relative to the fringe pattern provides information as to the position of the defect on said surface.

49. The process of claim 48 which includes the step of continuously recording and/or displaying information as to the position of each defect on said surface.

50. The process of claim 43 wherein the presence of a defect at a given distance of displacement of said smooth surface relative to the fringe pattern provides information as to the position of the defect on said surface.

51. The process of claim 50 which includes the step of continuously recording and/or displaying information as to the position of each defect on said surface.

52. The process of claim 29 wherein the presence of a defect at a given distance of displacement of said smooth surface relative to the fringe pattern provides information as to the position of the defect on said surface.

53. The process of claim 52 which includes the step of continuously recording and/or displaying information as to the position of each defect on said surface.

54. The process of claim 29 wherein said smooth surface is tilted around the y axis through a degree of arc sufficient to ensure that substantially all specularly-reflected radiation bypasses the receiver of the backscattered optical radiation.

55. A system for sensing the effective magnitude and/or number and/or spatial distribution of individual defects on a high-precision smooth surface of an article which may have said defects randomly distributed and relatively spatially-distant each from the other and which additionally may have relatively spatially-distant rough spots comprising adjacent, randomly-distributed defects comprising:

a. means for producing a pair of coherent optical radiation beams of substantially the same size and intensity, one of said beams having a different frequency from said other beam, the difference in frequency being within the radio frequency range;

b. means for converging said beams to form a laterally-moving fringe pattern;

c. means for adjusting the cross-sectional area of the fringe pattern so that it is substantially smaller than said smooth surface and no larger than an area which includes about an average predetermined spatial incidence of about one defect per pattern area on said surface;

d. means for adjusting the fringe period of the pattern to a width that is substantially wider than the effective cross-sectional dimension of a predetermined, maximum size defect as indicated by backscatter signal magnitude;

e. means for positioning at least the portion of said article bearing said smooth surface within the fringe pattern in such manner that said surface lies substantially in a plane defined by the $x$ and $y$ axes of the fringe pattern and the angle of incidence of the bisector of the pair of converging beams forming the fringe pattern is at an angle relative to said surface at the point of incidence such as to provide an angle of specular reflection, whereby substantially all specularly-reflected radiation bypasses means for receiving the backscattered optical radiation;

f. means for continuously spatially displacing the interference zone and/or said smooth surface relative to each other while maintaining the relative orientation of said fringe pattern substantially as defined in (e) supra;

g. means for continuing said relative displacement in such manner that substantially the entire predetermined area of said surface can be scanned by said fringe pattern;

h. means for continuously sensing the backscatter radiation from said surface;

i. means for continuously determining the amplitude of the AC signal;

j. means for continuously recording and/or displaying information as to the magnitude of the AC signal;

k. means for continuously recording and/or displaying information as to the number of said defects on said smooth surface; and l. means for continuously recording and/or displaying information as to the position of each defect on said surface.

56. The system of claim 55 which includes means for comparing the amplitude of the AC signal with a predetermined magnitude of AC signal.

57. The system of claim 56 which includes means for tilting said smooth surface around the $y$ axis through a degree of arc sufficient to ensure that substantially all specularly-reflected radiation bypasses the receiver of the backscattered optical radiation.

58. The system of claim 55 which includes means for continuously recording and/or displaying information as to the number of defects within given ranges of amplitude of said AC signal.

59. The system of claim 58 which includes means for tilting said smooth surface around the $y$ axis through a degree of arc sufficient to ensure that substantially all specularly-reflected radiation bypasses the receiver of the backscattered optical radiation.

60. The system of claim 55 which includes means for continuously determining the magnitude of the DC signal.

61. The system of claim 57 which includes means for continuously recording and/or displaying information as to the magnitude of the DC signal.

62. The system of claim 61 which includes means for determining the AC/DC signal ratio.

63. The system of claim 62 which includes means for tilting said smooth surface around the $y$ axis through a degree of arc sufficient to ensure that substantially all specularly-reflected radiation bypasses the receiver of the backscattered optical radiation.

64. The system of claim 61 which includes means for tilting said smooth surface around the $y$ axis through a degree of arc sufficient to ensure that substantially all specularly-reflected radiation bypasses the receiver of the backscattered optical radiation.

65. The system of claim 57 which includes means for determining the AC/DC signal ratio.

66. The system of claim 65 which includes means for tilting said smooth surface around the $y$ axis through a degree of arc sufficient to ensure that substantially all specularly-reflected radiation bypasses the receiver of the backscattered optical radiation.

67. The system of claim 60 which includes means for tilting said smooth surface around the $y$ axis through a degree of arc sufficient to ensure that substantially all specularly-reflected radiation bypasses the receiver of the backscattered optical radiation.

68. The system of claim 55 which includes means for tilting said smooth surface around the $y$ axis through a degree of arc sufficient to ensure that substantially all specularly-reflected radiation bypasses the receiver of the backscattered optical radiation.

* * * * *

UNITED STATES PATENT OFFICE
CERTIFICATE OF CORRECTION

Patent No. 4,030,830      Dated June 21, 1977

Inventor(s) Sandor Holly

It is certified that error appears in the above-identified patent and that said Letters Patent are hereby corrected as shown below:

Column 8, line 50, after "varied" insert -- by varying --.

Column 16, line 21, "Claim 57" should read -- Claim 60 --.

Column 16, line 36, "Claim 57" should read -- Claim 60 --.

Signed and Sealed this

Twenty-seventh Day of June 1978

[SEAL]

Attest:

RUTH C. MASON  
*Attesting Officer*

DONALD W. BANNER  
*Commissioner of Patents and Trademarks*